US012807520B2

(12) United States Patent
Lee

(10) Patent No.: US 12,807,520 B2
(45) Date of Patent: Nov. 24, 2026

(54) FLUID TREATMENT DEVICE

(71) Applicant: SEOUL VIOSYS CO., LTD., Ansan-si (KR)

(72) Inventor: Chung Hoon Lee, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 823 days.

(21) Appl. No.: 18/025,651

(22) PCT Filed: Sep. 10, 2021

(86) PCT No.: PCT/KR2021/012363
§ 371 (c)(1),
(2) Date: Mar. 10, 2023

(87) PCT Pub. No.: WO2022/055306
PCT Pub. Date: Mar. 17, 2022

(65) Prior Publication Data

US 2023/0339784 A1 Oct. 26, 2023

Related U.S. Application Data

(60) Provisional application No. 63/077,402, filed on Sep. 11, 2020.

(51) Int. Cl.
*C02F 1/32* (2023.01)
*A61L 9/20* (2006.01)
*C02F 1/00* (2023.01)

(52) U.S. Cl.
CPC ................ *C02F 1/32* (2013.01); *A61L 9/20* (2013.01); *C02F 1/001* (2013.01);
(Continued)

(58) Field of Classification Search
CPC .... A61L 9/02; A61L 2209/12; A61L 2209/14; C02F 1/001; C02F 1/32;
(Continued)

(56) References Cited

U.S. PATENT DOCUMENTS

2005/0129591 A1 6/2005 Wei et al.

FOREIGN PATENT DOCUMENTS

CN 206320874 U * 7/2017 ............... F24F 8/26
EP 1 946 781 B1 4/2014
(Continued)

OTHER PUBLICATIONS

KR20180115978A—EPO Machine Translation (Year: 2026).*
(Continued)

*Primary Examiner* — Patrick Orme
(74) *Attorney, Agent, or Firm* — Oblon, McClelland, Maier & Neustadt, L.L.P.

(57) ABSTRACT

A fluid treatment apparatus including: a pipe having an inlet and an outlet through which a fluid is configured to pass, and a flow channel connecting the inlet to the outlet to define a sterilization area; a fan to control a flow of the fluid; and at least one light source module including a light source to emit sterilizing light towards the sterilization area of the pipe and a substrate, in which the inlet and the outlet of the pipe are disposed adjacent to bottom and top surfaces of an external space of the pipe, respectively, the pipe includes a bent portion such that a flow direction of the fluid passing through the inlet and the outlet of the pipe is different from a flow direction of the fluid passing through sterilization area, and a length of the sterilization area is greater than a diameter of the sterilization area.

20 Claims, 8 Drawing Sheets

(52) U.S. Cl.
CPC ....... *A61L 2209/12* (2013.01); *A61L 2209/14* (2013.01); *C02F 2201/3227* (2013.01); *C02F 2201/3228* (2013.01); *C02F 2301/02* (2013.01); *C02F 2303/04* (2013.01)

(58) Field of Classification Search
CPC ...... C02F 2201/3227; C02F 2201/3228; C02F 2301/02; C02F 2303/04; F24F 8/22
See application file for complete search history.

(56) References Cited

FOREIGN PATENT DOCUMENTS

| | | | | |
|---|---|---|---|---|
| GB | 2515842 A | | 1/2015 | |
| KR | 10-2009-0081659 | | 7/2009 | |
| KR | 10-2013-0017998 | | 2/2013 | |
| KR | 10-1336590 | | 12/2013 | |
| KR | 10-2018-0115978 | | 10/2018 | |
| KR | 20180115978 A | * | 10/2018 | ................ C02F 1/32 |
| KR | 10-2019-0097435 | | 8/2019 | |
| WO | WO 00/06209 A2 | | 2/2000 | |

OTHER PUBLICATIONS

CN206320874U—EPO Machine Translation (Year: 2026).*
Partial Supplementary European Search Report issued Sep. 10, 2024 in European Patent Application No. 21867171.7, 13 pages.
Extended European Search Report issued Jan. 20, 2025 in European Patent Application No. 21867171.7, 14 pages.
International Search Report dated Dec. 30, 2021 in International Application No. PCT/KR2021/012363 (with English Translation).
Written Opinion dated Dec. 30, 2021 for International Patent Application No. PCT/KR2021/012363.

* cited by examiner

FLUID TREATMENT DEVICE

CROSS REFERENCE TO RELATED APPLICATIONS

This application is a National Stage Entry of International Application No. PCT/KR2021/012363, filed on Sep. 10, 2021, which claims priority from and the benefit of U.S. Provisional Application No. 63/077,402, filed on Sep. 11, 2020, each of which is incorporated by reference for all purposes as if fully set forth herein.

BACKGROUND

Field

Exemplary embodiments of the invention relate generally to a fluid treatment device.

Discussion of the Background

In recent years, as environmental pollution due to industrialization and large-scale infectious diseases has increased, interests in personal and public hygiene have also increased. Accordingly, as demand for sterilized water or purified air is increasing, sterilization-related products capable of creating a safe environment free from pathogenic microorganisms are being developed.

In a typical air purifier, the capacity may need to be changed according to a purification amount of air or a purification target area, which creates a problem in that the size of the air purifier needs to be increased with increasing capacity thereof.

The above information disclosed in this Background section is only for understanding of the background of the inventive concepts, and, therefore, it may contain information that does not constitute prior art.

SUMMARY

Exemplary embodiments provide a fluid treatment device capable of improving sterilization efficiency.

Exemplary embodiments also provide a fluid treatment device capable of performing sterilization without deterioration in sterilization efficiency even with increase in the amount of fluid and in area of a fluid treatment space.

Additional features of the inventive concepts will be set forth in the description which follows, and in part will be apparent from the description, or may be learned by practice of the inventive concepts.

In accordance with one aspect of the present disclosure, there is provided a fluid treatment device including: a pipe having an inlet and an outlet through which a fluid passes, the pipe being formed with a flow channel connecting the inlet to the outlet to define a sterilization area therein; a fan controlling flow of the fluid to force the fluid to flow from the inlet of the pipe to the outlet thereof; and at least one light source module including a light source emitting sterilizing light towards the sterilization area of the pipe and a substrate on which the light source is mounted. The inlet of the pipe may be disposed adjacent to a bottom surface of an external space of the pipe, the outlet of the pipe may be disposed adjacent to a top surface of the external space, the pipe may include a bent portion such that a flow direction of the fluid passing through the inlet and the outlet of the pipe is different from a flow direction of the fluid passing through the sterilization area, and a length of the sterilization area may be greater than a diameter of the sterilization area.

The pipe may be bent between the inlet and the sterilization area and between the sterilization area and the outlet.

The light source module may be disposed on at least one of an inner wall of the pipe facing the sterilization area between the inlet and the sterilization area and an inner wall of the pipe facing the sterilization area between the sterilization area and the outlet.

The substrate of the light source module may be disposed across the flow channel of the pipe, the light source of the light source module may emit light in a direction opposite to a flow direction of the fluid, and the fluid may pass through a passage formed by the substrate to flow towards the outlet of the pipe.

The light source module may be provided to the sterilization area to be disposed on at least one of an upper inner wall and a lower inner wall of the pipe defining the sterilization area.

The pipe may further include at least one guide formed in the sterilization area to change a flow path of the fluid and the guide may be formed on an upper inner wall of the pipe to extend downwards therefrom or on a lower inner wall of the pipe to extend upwards therefrom.

The guide may be provided in plural to the pipe and the sterilization area may be alternately provided with the guide formed on the upper inner wall of the pipe and the guide formed on the lower inner wall of the pipe.

The guide may have an outer surface closely contacting the inner wall of the pipe defining the sterilization area and may be formed with multiple through-holes penetrating opposite surfaces thereof, and the fluid may pass through the through-holes of the guide.

The guide may be provided in plural to the pipe and may be disposed such that the through-holes of one guide alternate with the through-holes of another guide.

The guide may be formed of a light transmitting material.

The substrate of the light source module may be disposed across the flow channel of the pipe, the light source of the light source module may emit light in a direction opposite to a flow direction of the fluid, and the fluid passes through a passage formed by the substrate to flow towards the outlet of the pipe.

The fluid treatment device may further include a filter formed on the guide and filtering out contaminants in the fluid.

The light source module may be disposed at each of both sides of the guide.

The sterilization area of the pipe may have a larger cross-sectional area than the inlet and the outlet of the pipe.

The pipe may be provided in plural and the outlet of one pipe is connected to the inlet of another pipe.

The pipe may include at least two bent portions each having a curved surface on at least a portion of an inner wall thereof, the sterilization area may be formed between the two bent portions, and the light source module may be placed diagonally on the curved surface to emit light towards the sterilization area.

The light source module may further include a substrate holder securing the substrate to the curved surface in a diagonal direction and the substrate holder may include one portion secured to the curved surface of the pipe and another portion on which the substrate is mounted.

The one portion and the other portion of the substrate holder may allow angle adjustment.

The fan may be disposed near the inlet of the pipe.

The fluid treatment device may further include a filter disposed on at least one of a front end and a rear end of the fan.

It is to be understood that both the foregoing general description and the following detailed description are illustrative and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate illustrative embodiments of the invention, and together with the description serve to explain the inventive concepts.

DETAILED DESCRIPTION

Figure 1:
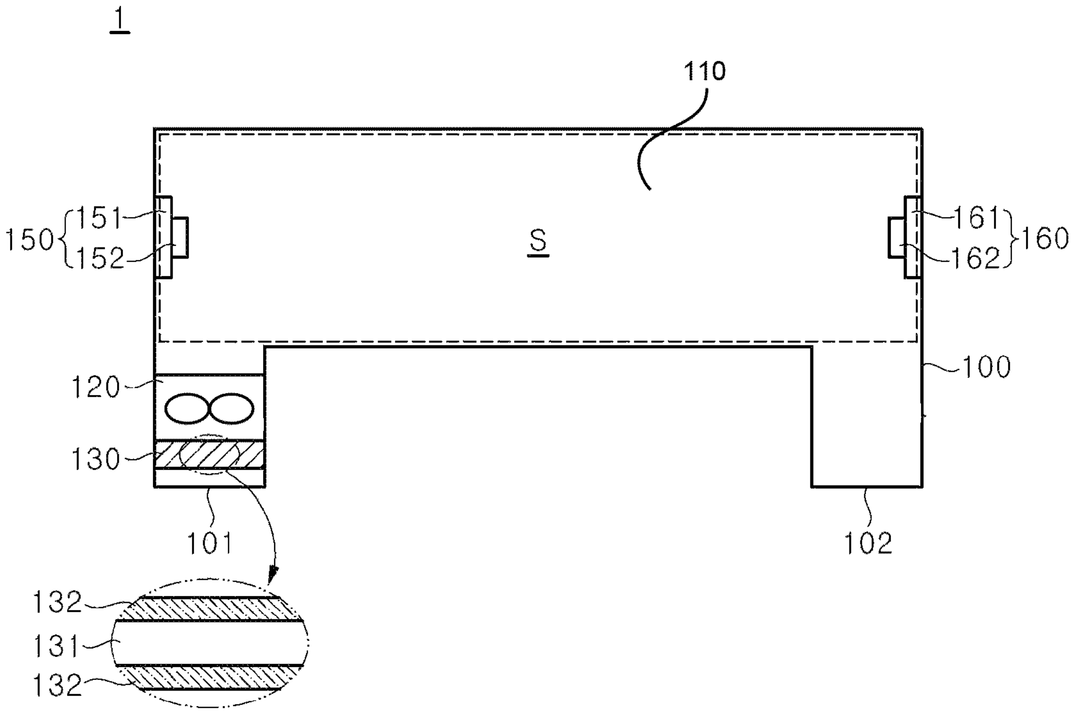
FIG. 1 is a view of a fluid treatment apparatus according to a first exemplary embodiment.

In the following description, for the purposes of explanation, numerous specific details are set forth in order to provide a thorough understanding of various embodiments or implementations of the invention. As used herein "embodiments" and "implementations" are interchangeable words that are non-limiting examples of devices or methods employing one or more of the inventive concepts disclosed herein. It is apparent, however, that various embodiments may be practiced without these specific details or with one or more equivalent arrangements. In other instances, well-known structures and devices are shown in block diagram form in order to avoid unnecessarily obscuring various embodiments. Further, various embodiments may be different, but do not have to be exclusive. For example, specific shapes, configurations, and characteristics of an embodiment may be used or implemented in another embodiment without departing from the inventive concepts.

Unless otherwise specified, the illustrated embodiments are to be understood as providing illustrative features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath"

other elements or features would then be oriented "above" the other elements or features. Thus, the term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various embodiments are described herein with reference to sectional and/or exploded illustrations that are schematic illustrations of idealized embodiments and/or intermediate structures. As such, variations from the shapes of the illustrations as a result, for example, of manufacturing techniques and/or tolerances, are to be expected. Thus, embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

FIG. 1 is a view of a fluid treatment apparatus according to a first exemplary embodiment.

A fluid treatment apparatus 1 according to the first exemplary embodiment may include a pipe 100, a fan 120, a filter 130, a first light source module 150, and a second light source module 160.

Referring to FIG. 1, the pipe 100 is formed with a flow channel 110 defining a path through which a fluid introduced into the pipe 100 flows. In addition, the pipe 100 may include an inlet 101 corresponding to a path through which the fluid flows into the flow channel 110 from outside of the pipe 100, and an outlet 102 corresponding to a path through which the fluid is discharged from the flow channel 110 to the outside of the pipe 100.

Referring to FIG. 1, the inlet 101 and the outlet 102 are placed below the sterilization area S. However, the inventive concepts are not limited thereto. For example, the inlet 101 may be placed below a fluid treatment space and the outlet 102 may be placed above the fluid treatment space in other exemplary embodiments. More particularly, in the fluid treatment apparatus 1, the inlet 101 and the outlet 102 that are shown in the drawings as facing downwards may not need to be arranged in the fluid treatment space. A structure in which the fluid treatment apparatus 1 is disposed in the fluid treatment space will be described in detail in other exemplary embodiments described below.

An inner wall of the pipe 100 may include a material that reflects light. For example, a light reflective material may be coated on the inner wall of the pipe 100. Alternatively, the pipe 100 may be formed of a light reflective material or a material including a light reflective material. In addition, the entire inner wall of the pipe 100 may include a light reflective material. Alternatively, the light reflective material may be present only on the inner wall defining a sterilization area S in which sterilization of the fluid is performed.

The first light source module 150 and the second light source module 160 may be disposed in the flow channel 110 of the pipe 100.

The first light source module 150 and the second light source module 160 may be disposed on the inner wall of the pipe 100 to emit light for treatment of the fluid towards the fluid flowing in the flow channel 110. Here, the sterilization area S refers to a region in which sterilization of the fluid is performed by light emitted from the first light source module 150 and the second light source module 160. That is, the fluid may be sterilized by light emitted from at least one of the first light source module 150 and the second light source module 160 while the fluid passes through the sterilization area S. More particularly, the first light source module 150 and the second light source module 160 emit sterilizing light, which is light having a wavelength capable of sterilizing the fluid. For example, the sterilizing light may be ultraviolet light. However, the inventive concepts are not limited thereto, and the kind of sterilizing light may be changed according to the kind of fluid and the sterilization purpose in other exemplary embodiments.

In addition, each of the first light source module 150 and the second light source module 160 may include at least one light source 152, 162 that generates and emits light and a substrate 151, 161 on which the light source 152, 162 is mounted. The first light source module 150 and the second light source module 160 may emit different kinds of light. Alternatively, each of the first light source module 150 and the second light source module 160 may include multiple light sources 152, 162, which emit the same or different kinds of light.

The first light source module 150 may be placed on the inner wall of the pipe 100 facing the sterilization area S between the inlet 101 and the sterilization area S. In addition, the second light source module 160 may be placed on the inner wall of the pipe 100 facing the sterilization area S between the sterilization area S and the outlet 102. Accordingly, as shown in FIG. 1, the first light source module 150 and the second light source module 160 may face each other at opposite ends of the sterilization area S. That is, both the first light source module 150 and the second light source module 160 may emit sterilizing light in a longitudinal direction of the sterilization area S.

Accordingly, the first light source module 150 may emit light in the same direction as a flow direction of the fluid. In addition, the second light source module 160 may emit light in a direction opposite to the flow direction of the fluid.

According to the illustrated exemplary embodiment, the pipe 100 may have a structure in which a length of the flow channel 110 is greater than a diameter of the flow channel 110.

In the fluid treatment apparatus 1 according to the illustrated exemplary embodiment, the sterilization area S can be maximized by the structure, in which the flow channel 110 of the pipe 100 extends to have a long length in the longitudinal direction and the first light source module 150 and the second light source module 160 are disposed at opposite ends of the flow channel 110, respectively.

In the fluid treatment apparatus 1 according to this exemplary embodiment, the amount of the fluid that can be simultaneously sterilized is increased due to the structure that maximizes the sterilization area S, thereby improving sterilization efficiency with respect to the fluid. In addition, in the fluid treatment apparatus 1 according to this exemplary embodiment, since the sterilization area S has a long length, it is possible to increase a residence time of the fluid in the sterilization area S while passing therethrough, thereby improving sterilization efficiency with respect to the fluid.

The fan 120 may be disposed inside and outside the pipe 100. In addition, the fan 120 may be disposed near at least one of the inlet 101 and the outlet 102. In FIG. 1, the fan 120 is placed near the inlet 101 inside the pipe 100. However, the inventive concepts are not limited thereto, and the arrangement and the number of fans may be changed in various ways so long as the fans 120 can generate flow of the fluid, such that the fluid passes through the sterilization area S inside the pipe 100.

In addition, the fan 120 may control a flow rate of the fluid. The fluid treatment apparatus 1 according to this exemplary embodiment may control the flow rate of the fluid by changing a rotation speed of the fan 120, the number of fans 120 operated, and the like.

The fluid treatment apparatus 1 according to this exemplary embodiment can improve sterilization efficiency by controlling the flow rate of the fluid passing through the sterilization area S using the fan 120.

As such, the fluid treatment apparatus 1 according to this exemplary embodiment may control the amount and flow rate of the fluid passing through the sterilization area S by adjusting the fan 120 and the length of the sterilization area S. Accordingly, the fluid treatment apparatus 1 according to this exemplary embodiment can improve sterilization efficiency with respect to the fluid by sufficiently irradiating the fluid passing through the pipe 100 with light, such that contaminants in the fluid sufficiently react with the light.

The fluid treatment apparatus 1 according to this exemplary embodiment may further include at least one filter 130.

Referring to FIG. 1, the filter 130 may be disposed between the fan 120 and the inlet 101. In this structure, some contaminants in the fluid may be primarily filtered out by the filter 130. Accordingly, the filter 130 of the fluid treatment apparatus 1 according to this exemplary embodiment minimizes contamination of the fan 120 by the contaminants in the fluid.

Although the filter 130 is disposed between the fan 120 and the inlet 101 in FIG. 1, the inventive concepts are not limited thereto. In some exemplary embodiments, the filter 130 may be provided to at least one of a front end and a rear end of the fan 120. In addition, for the fluid treatment apparatus including multiple filters 130, the filters 130 may be different types of filters 130.

In addition, the filter 130 may include multiple layers of different materials. For example, the filter 130 may include a first filter layer 131 and a second filter layer 132.

The first filter layer 131 may have multiple orifices having a smaller size than contaminants in the fluid. Accordingly, the first filter layer 131 may filter out the contaminants while allowing the fluid to pass therethrough.

The second filter layer 132 may be formed of a different material than the first filter layer 131. The second filter layer 132 may be formed of a material having better rigidity or hardness than the first filter layer 131.

The second filter layer 132 may be formed on at least one of the front end and the rear end of the first filter layer 131 to prevent the first filter layer 131 from being damaged by the fluid flowing at a fast speed.

The concentration of contaminants in the fluid passing through the sterilization area S can be reduced by the filter 130.

Since the concentration of contaminants to be sterilized by light is reduced by the filter 130, the fluid treatment apparatus 1 according to this exemplary embodiment can improve sterilization efficiency with respect to the fluid for the same exposure time and the same quantity of light.

Next, a fluid treatment apparatus according to a second exemplary embodiment will be described. Here, the following description will be focused on different features from those of the fluid treatment apparatus 1 according to the first exemplary embodiment. For details of omitted or briefly described features, refer to the above description.

Figure 2:
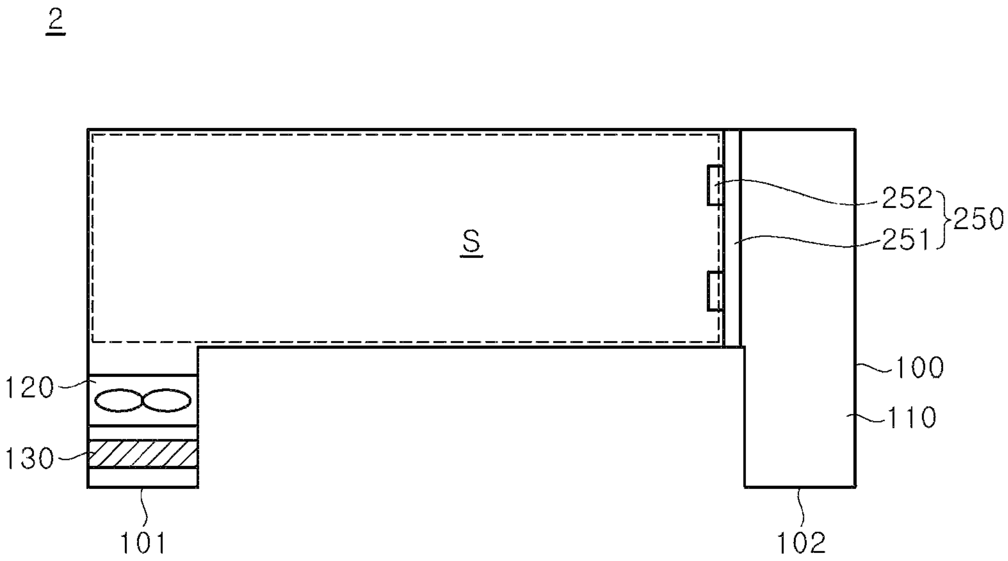
FIG. 2 is a view of a fluid treatment apparatus according to a second exemplary embodiment.

FIG. 2 is a view of a fluid treatment apparatus according to a second exemplary embodiment.

A fluid treatment apparatus 2 according to the second exemplary embodiment may include a pipe 100, a fan 120, a filter 130, and a light source module 250.

The light source module 250 may include a substrate 251 and multiple light sources 252 mounted on the substrate 251.

According to this exemplary embodiment, the substrate 251 may have a length similar to the diameter of the flow channel 110. Accordingly, as shown in FIG. 2, the substrate 251 may be secured inside the pipe 100 to be disposed across the flow channel 110.

According to this exemplary embodiment, the substrate 251 does not close the flow channel 110. That is, the substrate 251 may have a smaller cross-sectional area than the flow channel 110. Thus, the substrate 251 may be provided at opposite sides flow channel 110 with spaces through which a fluid passes, respectively. For example, the opposite sides of the substrate 251 are separated from an inner wall of the pipe 100 to allow the fluid to pass through the spaces defined between the substrate 251 and the inner wall of the pipe 100. Alternatively, the substrate 251 may be formed with multiple through-holes formed through upper and lower surfaces thereof, and may have an outer periphery closely contacting the inner wall of the pipe 100. In this structure, the fluid passes through the through-holes of the substrate 251.

With this structure, the substrate 251 may function to guide the flow of the fluid.

In addition, since the substrate 251 is formed to block a part of a path through which the fluid moves, some of the fluid can collide with the substrate 251. Thus, a residence time of the fluid around the substrate 251 can increase. As the residence time of the fluid around the substrate 251 increases, an exposure time of the fluid to light emitted from the light source module 250 also increases.

The light sources 252 mounted on the substrate 251 may emit light in a direction opposite to a flow direction of the fluid.

Accordingly, the fluid can be continuously exposed to light from a start point of the sterilization area S until the fluids passes through the substrate 251.

As such, the fluid treatment apparatus 2 according to this exemplary embodiment can increase the exposure time of the fluid to light through the structure of the substrate 251 in the light source module 250 and arrangement of the light source module 250, thereby improving sterilization efficiency.

FIG. 2 shows that the fluid treatment apparatus 2 includes a single light source module 250. Alternatively, the fluid treatment apparatus 2 may include multiple light source modules 250. That is, multiple substrates 251 each having the light source 252 thereon may be mounted on the pipe 100. In this manner, a collision frequency between the fluid and the substrate 251 increases, whereby the exposure time of the fluid to light also increases, thereby further improving sterilization efficiency with respect to the fluid.

Figure 3:
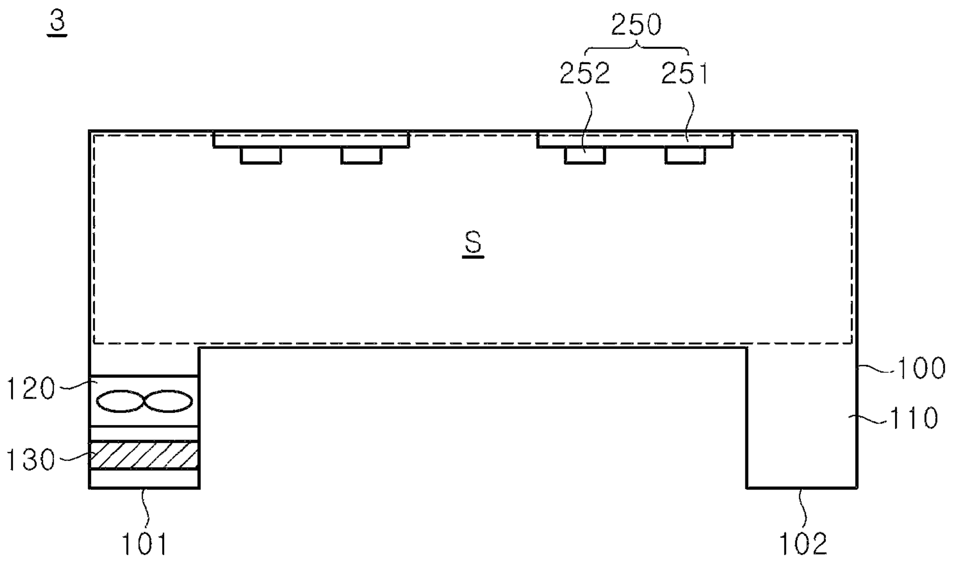
FIG. 3 is a view of a fluid treatment apparatus according to a third exemplary embodiment.

FIG. 3 is an exemplary view of a fluid treatment apparatus according to a third exemplary embodiment.

According to the third exemplary embodiment, a fluid treatment apparatus 3 may include a pipe 100, a fan 120, a filter 130, and a light source module 250. The light source module 250 may include a substrate 251 and multiple light sources 252 mounted on the substrate 251.

Referring to FIG. 3, in the fluid treatment apparatus 3 according to the third exemplary embodiment, the light source module 250 is placed in the sterilization area S. In addition, the light source module 250 may be mounted on the pipe 100, such that a lower surface of the substrate 251 faces an inner wall of the pipe 100. Here, the lower surface of the substrate 251 is an opposite surface to the surface of the substrate 251 on which the light sources 252 are mounted. That is, the light sources 252 are mounted on an upper surface of the substrate 251.

Referring to FIG. 3, the light source module 250 is placed at an upper portion of the sterilization area S. Alternatively, the light source module 250 may be placed at a lower portion of the sterilization area S. In addition, the light source module 250 may be placed at each of the upper and lower portions of the sterilization area S.

According to this exemplary embodiment, since the light source module 250 is placed above the flow channel 110, a distance between the light source module 250 and the fluid is shorter than in the above exemplary embodiments. That is, a light irradiation distance of the light source module 250 can be reduced. A shorter light irradiation distance provides higher light intensity.

That is, the fluid treatment apparatus 3 according to this exemplary embodiment can increase the intensity of light emitted to the fluid by reducing the distance between the light source module 250 and the fluid.

Accordingly, the fluid treatment apparatus 3 according to this exemplary embodiment can improve sterilization efficiency with respect to the fluid by increasing the intensity of light emitted to the fluid.

The fluid treatment apparatus 3 according to this exemplary embodiment may include multiple light source modules 250. In the fluid treatment apparatus 3 according to this exemplary embodiment, the multiple light source modules 250 may be arranged along the pipe 100, thereby further improving sterilization efficiency.

Figure 4:
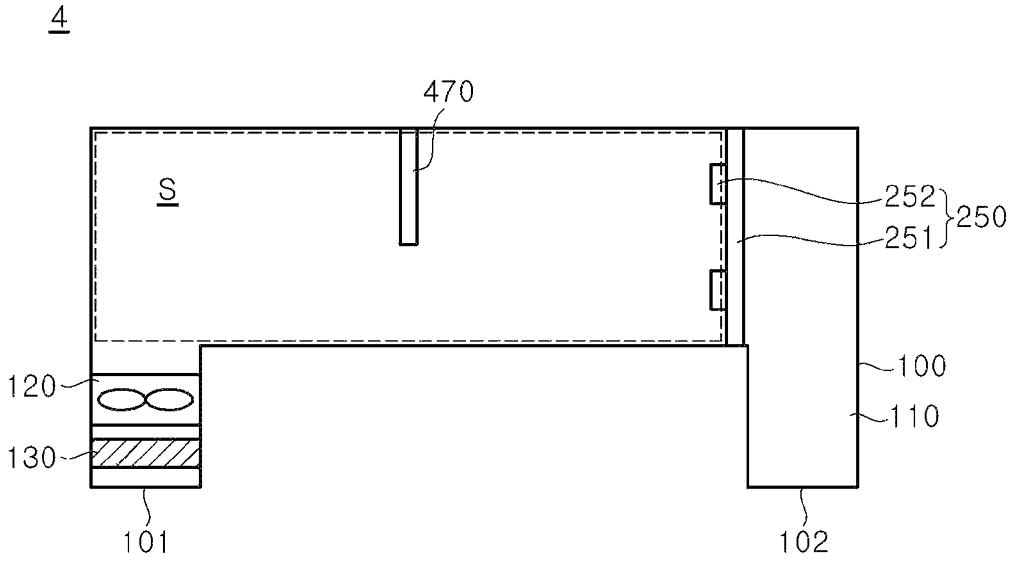
FIG. 4 is a view of a fluid treatment apparatus according to a fourth exemplary embodiment.

FIG. 4 is a view of a fluid treatment apparatus according to a fourth exemplary embodiment.

A fluid treatment apparatus 4 according to the fourth exemplary embodiment may include a pipe 100, a fan 120, a filter 130, a guide 470, and a light source module 250. The light source module 250 may include a substrate 251 and multiple light sources 252 mounted on the substrate 251.

The light source module 250 may be disposed across the flow channel 110 and may emit light in a direction opposite to the flow direction of the fluid. That is, the light source module 250 according to this exemplary embodiment may be the same as the light source module 250 according to the second exemplary embodiment.

According to this exemplary embodiment, the guide 470 may be disposed in the sterilization area S. Referring to FIG. 4, the guide 470 may have a structure, in which one end of the guide 470 adjoins an upper inner wall of the pipe 100 and the other end of the guide 470 is separated from a lower inner wall of the pipe 100. Accordingly, the fluid passes through a lower space defined between the inner wall of the pipe 100 and the guide 470 while passing through the sterilization area S.

That is, some of the fluid may collide with the guide 470 while passing through sterilization area S. At this time, a vortex may be generated in the sterilization area S by the fluid colliding with the guide 470. The vortex increases the residence time of the fluid in the sterilization area S. For example, the speed of the fluid passing through the lower space below the guide 470 may be reduced by the vortex. Accordingly, the exposure time of the fluid to light emitted from the light source module 250 can increase.

Further, according to the arrangement structure of the light source module 250, the fluid may be continuously exposed to light emitted from the light source module 250 in a region between the guide 470 and the light source module 250.

Further, when the guide 470 is formed of a light transmitting material, the fluid may be continuously exposed to light emitted from the light source module 250 while flowing in the sterilization area S.

Alternatively, the guide 470 may be formed of a light reflective material. The guide 470 formed of the light reflective material reflects sterilizing light such that the entirety of the sterilization area S can be uniformly irradiated with the light. As such, the guide 470 serves to improve irradiation uniformity in the sterilization area S while minimizing a region of the sterilization area S not irradiated with light, thereby improving sterilization efficiency of the fluid treatment apparatus 4.

Further, the fluid passes through a narrow space between the guide 470 and the inner wall of the pipe 100, and then passes through a space defined by the entirety of the inner wall of the pipe 100. That is, the flow rate of the fluid can decrease with increasing cross-sectional area of the flow channel 110 through which the fluid flows.

Further, the guide 470 may change a flow path of the fluid. That is, the guide 470 serves to increase a movement distance of the fluid in the sterilization area S. Accordingly, the exposure time of the fluid to light can increase with increasing movement distance of the fluid in the sterilization area S.

With the arrangement structure of the guide 470 and the light source module 250, the fluid treatment apparatus 4 according to this exemplary embodiment can improve sterilization efficiency with respect to the fluid by reducing the flow rate of the fluid while increasing the movement distance of the fluid, and continuously supplying light to the fluid during flow of the fluid.

Figure 5:
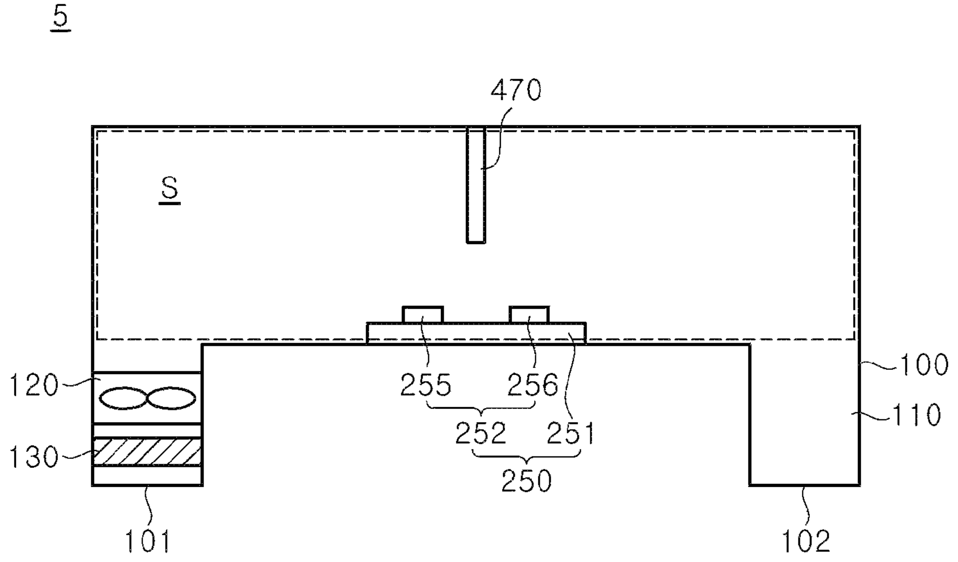
FIG. 5 is a view of a fluid treatment apparatus according to a fifth exemplary embodiment.

FIG. 5 is a view of a fluid treatment apparatus according to a fifth exemplary embodiment.

A fluid treatment apparatus 5 according to the fifth exemplary embodiment may include a pipe 100, a fan 120, a filter 130, a guide 470, and a light source module 250. The light source module 250 may include a substrate 251 and multiple light sources 252 mounted on the substrate 251.

The guide 470 may have a structure, in which one end of the guide 470 adjoins an upper inner wall of the pipe 100 and the other end of the guide 470 is separated from a lower inner wall of the pipe 100. Accordingly, the fluid passes through a lower space defined between the inner wall of the pipe 100 and the guide 470 while passing through the sterilization area S.

Referring to FIG. 5, the light source module 250 may be placed below the guide 470. In addition, the guide 470 may be mounted on the pipe 100 such that the lower surface of the substrate 251 faces the inner wall of the pipe 100.

Here, the light source module 250 may include multiple light sources 252, in which some light sources 252 are disposed between the inlet 101 and the guide 470 of the pipe 100 and the other light sources 252 are disposed between the guide 470 and the outlet 102. For example, a first light source 255 may be disposed between the inlet 101 and the guide 470, and a second light source 256 may be disposed between the guide 470 and the outlet 102.

In addition, some fluid collides with the guide 470 to generate a vortex in a region between the inlet 101 and the guide 470. Further, the fluid passes through a space between the narrow guide 470 and the pipe 100. Accordingly, the residence time of the fluid increases between the inlet 101 and the guide 470.

That is, the guide 470 allows the fluid residing in the region between the inlet 101 and the guide 470 to be exposed to light emitted from the first light source 255. Since the residence time of the fluid is increased by the guide 470, the exposure time of the fluid to light emitted from the first light source 255 can be increased in the region between the inlet 101 and the guide 470.

Further, the guide 470 serves to guide the fluid to move towards a wide space between the guide 470 and the outlet 102 after passing through a narrow space. Here, the flow rate of the fluid decreases with increasing cross-sectional area of the flow channel 110. Accordingly, the fluid may be exposed to light emitted from the second light source 256 in the region between the guide 470 and the outlet 102. As such, the exposure time of the fluid to light emitted from the second light source 256 can be increased.

Although the guide 470 is illustrated as being disposed between the first light source 255 and the second light source 256 in this exemplary embodiment, in some exemplary embodiments, when the fluid treatment apparatus 5 includes multiple light source modules 250, the guide 470 may be disposed between the light source modules 250 instead of being disposed between the light sources 256.

Further, in this exemplary embodiment, the light source module 250 is disposed at a lower portion of the pipe 100 to reduce the light irradiation distance. That is, the distance between the light source module 250 and the fluid is decreased, thereby increasing irradiation intensity of light emitted to the fluid.

With the arrangement structure of the light source module 250 and the guide 470, the fluid treatment apparatus 5 according to this exemplary embodiment can improve sterilization efficiency with respect to the fluid by increasing the exposure time of the fluid to light and the irradiation intensity of light emitted to the fluid.

The fluid treatment apparatus 5 according to this exemplary embodiment may include multiple light source modules 250. As such, the fluid treatment apparatus 5 according to this exemplary embodiment increases the quantity of light emitted into the sterilization area S, thereby further improving sterilization efficiency with respect to the fluid.

Figure 6:
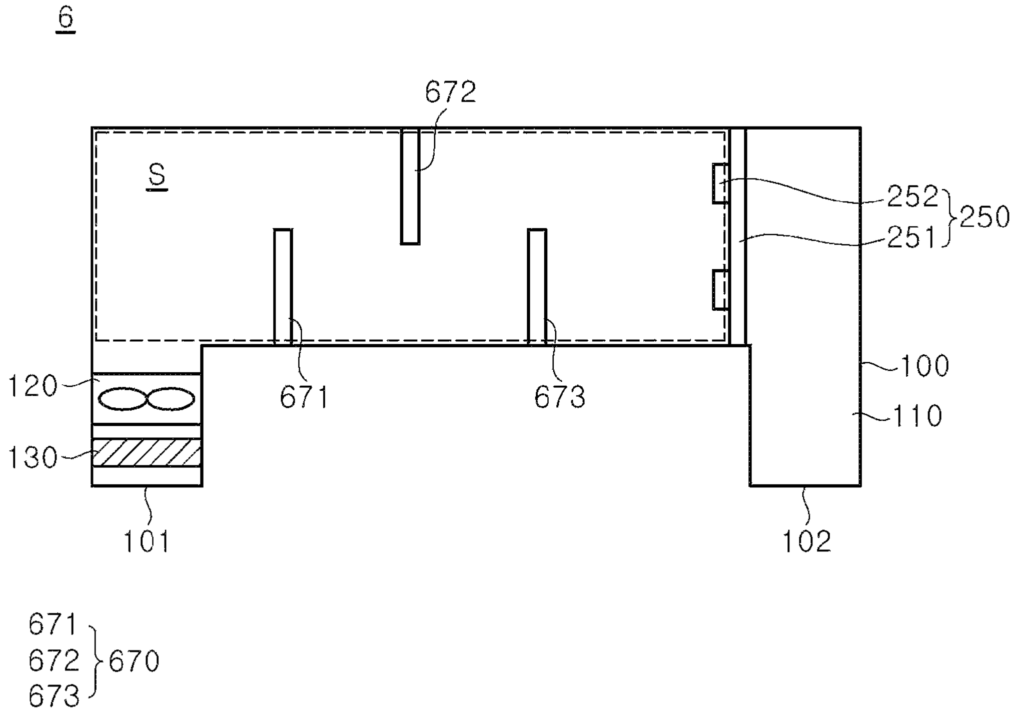
FIG. 6 is a view of a fluid treatment apparatus according to a sixth exemplary embodiment.

FIG. 6 is a view of a fluid treatment apparatus according to a sixth exemplary embodiment.

A fluid treatment apparatus 6 according to the sixth exemplary embodiment may include a pipe 100, a fan 120, a filter 130, guides 670, and a light source module 250. The light source module 250 may include a substrate 251 and multiple light sources 252 mounted on the substrate 251.

The light source module 250 may be disposed across the flow channel 110 and may emit light in a direction opposite to the flow direction of the fluid.

According to this exemplary embodiment, the sterilization area S may be provided with multiple guides 670. The multiple guides 670 may be formed on an upper or lower inner wall of the pipe 100.

Some of the guides 670 may extend downwards from the upper inner wall of the pipe 100. In addition, the other guides 670 may extend upwards from the lower inner wall of the pipe 100. The guides 670 formed on the upper inner wall of the pipe 100 and the guides 670 formed on the lower inner wall of the pipe 100 may be alternately arranged.

For example, the guides 670 may include a first guide 671, a second guide 672, and a third guide 673. Here, the first guide 671 and the third guide 673 are formed on the lower inner wall of the pipe 100, and the second guide 671 is formed on the upper inner wall of the pipe 100.

The fluid treatment apparatus 6 according to this exemplary embodiment can achieve improvement in sterilization efficiency as in the fluid treatment apparatus 4 shown in FIG. 4, which improves sterilization efficiency through the guide 470 and the light source module 250.

Furthermore, the fluid treatment apparatus 6 according to this exemplary embodiment can increase the flow path of the fluid in the sterilization area S through the multiple guides 670. Accordingly, the fluid treatment apparatus 6 according to this exemplary embodiment allows the fluid to flow along the flow path of the fluid defined by the multiple guides 670, thereby increasing the residence time of the fluid in the sterilization area S.

In addition, the flow rate of the fluid can be reduced due to collision of the fluid with the guides 670 while the fluid passes through the sterilization area S. That is, the residence time of the fluid in the sterilization area S can be increased due to collision of the fluid with the guides 670 while the fluid passes through the sterilization area S.

Further, the multiple guides 670 may be formed of a light transmitting material. For example, the guides 670 may be formed of a light transmitting material, such as glass, quartz, and the like.

Accordingly, light emitted from the light source module 250 passes through the multiple guides 670 and reaches the fluid passing through the sterilization area S.

The fluid treatment apparatus 6 according to this exemplary embodiment can increase the exposure time of the fluid to light by increasing the residence time of the fluid in the sterilization area S. Accordingly, the fluid treatment apparatus 6 according to this exemplary embodiment can improve sterilization efficiency through increase in exposure time of the fluid to light.

Figure 7:
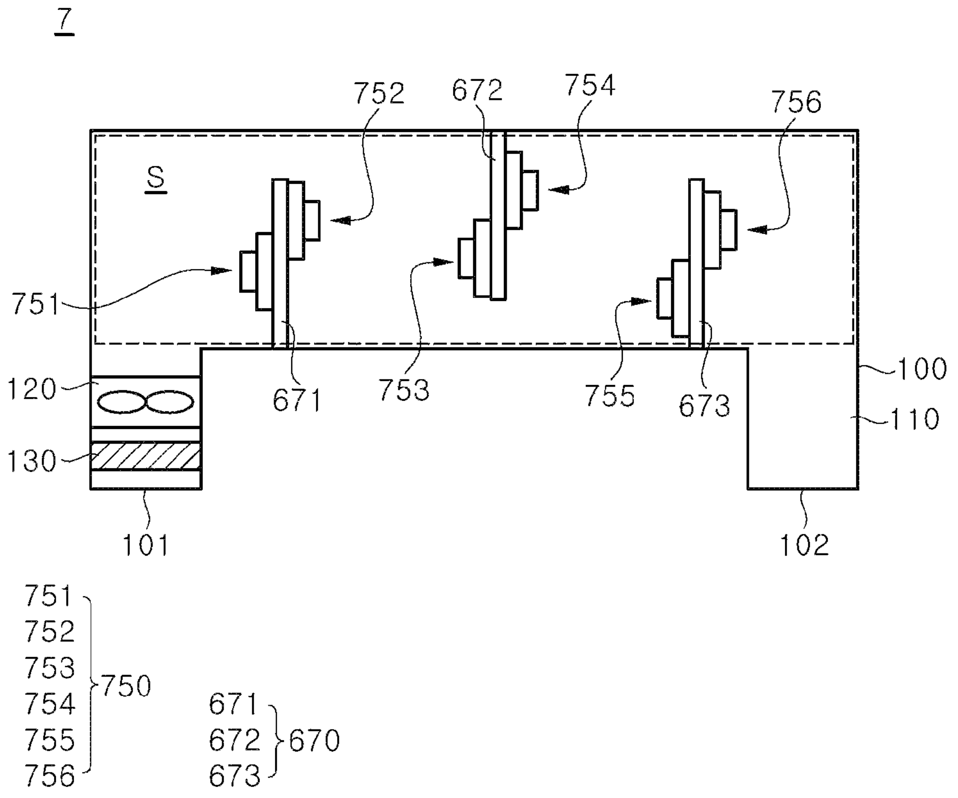
FIG. 7 is a view of a fluid treatment apparatus according to a seventh exemplary embodiment.

FIG. 7 is a view of a fluid treatment apparatus according to a seventh exemplary embodiment.

A fluid treatment apparatus 7 according to the seventh exemplary embodiment may include a pipe 100, a fan 120, a filter 130, guides 670, and light source modules 750. The light source module 750 may include a substrate and multiple light sources mounted on the substrate.

Referring to FIG. 7, the pipe 100 may be provided with multiple guides 670, each of which may be provided with multiple light source modules 750. In addition, the light source modules 750 may be disposed on opposite surfaces of the guide 670, respectively.

For example, the fluid treatment apparatus 7 may include first to third guides 671 to 673.

Referring to FIG. 7, the first guide 671 is a guide 670 disposed closest to the inlet 101 of the pipe 100 and the third guide 673 is a guide 670 disposed closest to the outlet 102 of the pipe 100. Each of the first guide 671 and the third guide 673 extends upwards from a lower inner wall of the pipe 100. The second guide 672 is disposed between the first guide 671 and the third guide 673. The second guide 672 extends downwards from an upper inner wall of the pipe 100.

Further, each of the first to third guides 671 to 673 may be provided with the light source modules 750.

Referring to FIG. 7, the first guide 671 may include a first-1 light source module 751 on one surface thereof, and a first-2 light source module 752 on the other surface thereof. In addition, the second guide 672 may include a second-1 light source module 753 on one surface thereof, and a second-2 light source module 754 on the other surface thereof. Further, the third guide 673 may include a third-1 light source module 755 on one surface thereof, and a third-2 light source module 756 on the other surface thereof.

Here, the one surface of the guide 670 refers to a surface facing in an opposite direction to the flow direction of the fluid. That is, the one surface of the guide 670 is a surface facing the flow flowing from the inlet 101 to the outlet 102. The other surface of the guide 670 is an opposite surface of the one surface of the guide 670.

The first-1 light source module 751 may emit light towards the fluid passing through a region from a start point of the sterilization area S to the first guide 671.

The third-2 light source module 756 may emit light towards the fluid passing through a region from the third guide 673 to an end portion of the sterilization area S.

The first-2 light source module 752 and the second-1 light source module 753 may emit light towards the fluid passing through a region between the first guide 671 and the second guide 672.

In addition, the second-2 light source module 754 and the third-1 light source module 755 may emit light towards the fluid passing through a region between the second guide 672 and the third guide 673.

As such, the fluid treatment apparatus 7 according to this with and on the other surface thereof with embodiment can increase the residence time of the fluid in the sterilization area S using the multiple guides 670.

Further, in the fluid treatment apparatus 7 according to this exemplary embodiment, the light source modules 750 are provided to the guides 670, whereby the distance from the light source modules 750 to the fluid passing through the sterilization area S can be reduced. That is, the fluid passing through the sterilization area S can be exposed to high intensity of light due to a close distance from the fluid to the light source modules 750.

The light source modules 750 disposed on the opposite surfaces of each of the guides 670 to face each other emit light towards the same region. Here, lights emitted from the light source modules 750 overlap each other.

In the fluid treatment apparatus 7 according to this exemplary embodiment, the light source modules 750 arranged to emit light towards the same region may be alternately arranged in consideration of a beam angle. That is, it is possible to achieve improvement in overall irradiation uniformity of the corresponding region through control of an irradiation overlapping region of light emitted from the light source modules 750.

For example, the first-2 light source module 752 and the second-1 light source module 753 may be alternately arranged in consideration of a beam angle. Here, the first-2 light source module 752 and the second-1 light source module 753 may be arranged to minimize the irradiation overlapping region of light emitted therefrom. Accordingly, the entire region between the first guide 671 and the second guide 672 can be uniformly irradiated with light emitted from the first-2 light source module 752 and the second-1 light source module 753. Such arrangement may also be applied to the second-2 light source module 754 and the third-1 light source module 755 to improve irradiation uniformity in a region between the second guide 672 and the third guide 673.

Although the light source modules 750 are illustrated as being respectively disposed on the opposite surfaces of each of the multiple guides 670 in the fluid treatment apparatus 7 according to this exemplary embodiment, the inventive concepts are not limited thereto.

In the fluid treatment apparatus 7 including the multiple guides 670 and the multiple light source modules 750, multiple light sources may be arranged on the upper and lower inner walls of the pipe 100 in the longitudinal direction of the pipe 100. Here, the light source modules 750 may be disposed between a start point of the sterilization area S and the first guide 670, between the last guide 670 and the end portion of the sterilization area S, and between adjacent guides 670.

Figure 8:
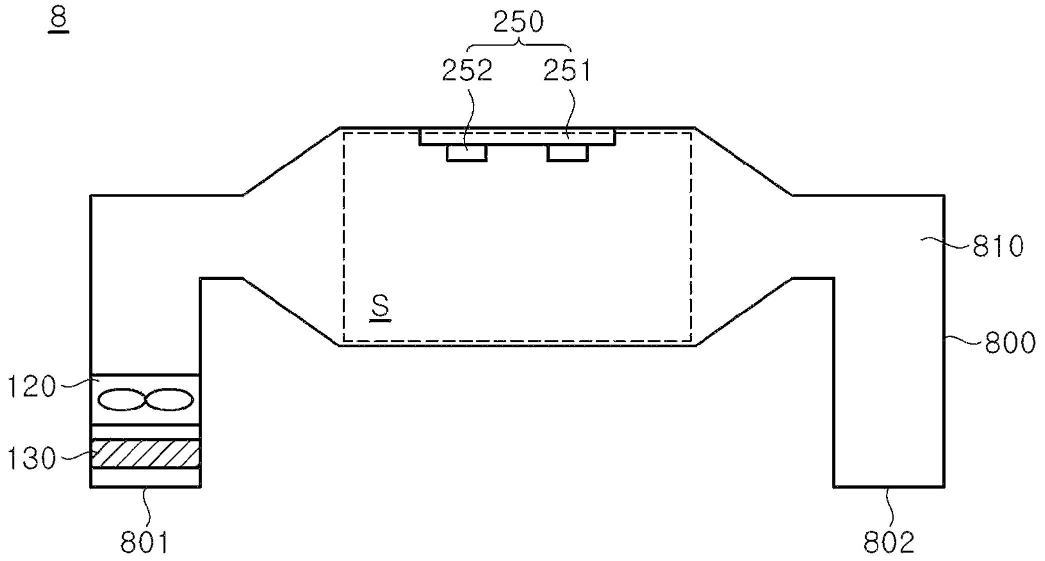
FIG. 8 is a view of a fluid treatment apparatus according to an eighth exemplary embodiment.

FIG. 8 is a view of a fluid treatment apparatus according to an eighth exemplary embodiment.

A fluid treatment apparatus 8 according to the eighth exemplary embodiment may include a pipe 810, a fan 120, a filter 130, and a light source module 250.

In the fluid treatment apparatus 8 according to this exemplary embodiment, the pipe 810 may have a structure, in which a portion of the pipe 810 has a different inner diameter than another portion thereof. That is, the pipe 810 may be formed such that a portion of a flow channel 810 has a different cross-sectional area than another portion thereof.

Referring to FIG. 8, the pipe 810 may have a structure, in which the sterilization area S has a greater diameter than an inlet 801 and an outlet 802. Furthermore, in the pipe 810, the sterilization area S may have a larger cross-sectional area than the inlet 801 and the outlet 802. Here, the cross-sectional area refers to an area of a cross-section of the pipe 810 taken in a vertical direction with respect to the flow direction of the fluid.

Here, the inlet 801 may have the same cross-sectional area as or a different cross-sectional area than the outlet 802.

The light source module 250 may be placed in the sterilization area S and may be disposed on the upper or lower inner wall of the pipe 810.

According to this exemplary embodiment, the fluid having passed through the inlet 801 can be reduced in flow rate as the cross-sectional area of the flow channel 810 increases. Accordingly, the flow rate of the fluid passing through the sterilization area S decreases, whereby the exposure time of the fluid to light emitted from the light source module 250 can be increased.

According to this exemplary embodiment, the fluid having passed through the sterilization area S flows towards the outlet 802 that has a smaller cross-sectional area than the fluid sterilization area S. Accordingly, the pipe 810 may have a structure, in which the cross-sectional area of the flow channel 810 becomes narrower toward the outlet 802 from the end portion of the sterilization area S. Here, some of the fluid flowing towards the outlet 802 may collide with the inner wall of the pipe 810 having a reduced diameter, instead of directly flowing towards the outlet 802. A vortex can be generated near the inner wall of the pipe 810 due to collision of the fluid with the inner wall of the pipe 810. As such, as the flow channel 810 has a gradually decreasing cross-sectional area, the residence time of the fluid in the pipe 810 increases, thereby increasing the exposure time of the fluid to light emitted from the light source module 250.

With the structure, in which a portion of the pipe has a different cross-sectional area than another portion thereof, the fluid treatment apparatus 8 according to this exemplary embodiment can improve sterilization efficiency by increasing the exposure time of the fluid to light emitted from the light source module 250.

Figure 9:
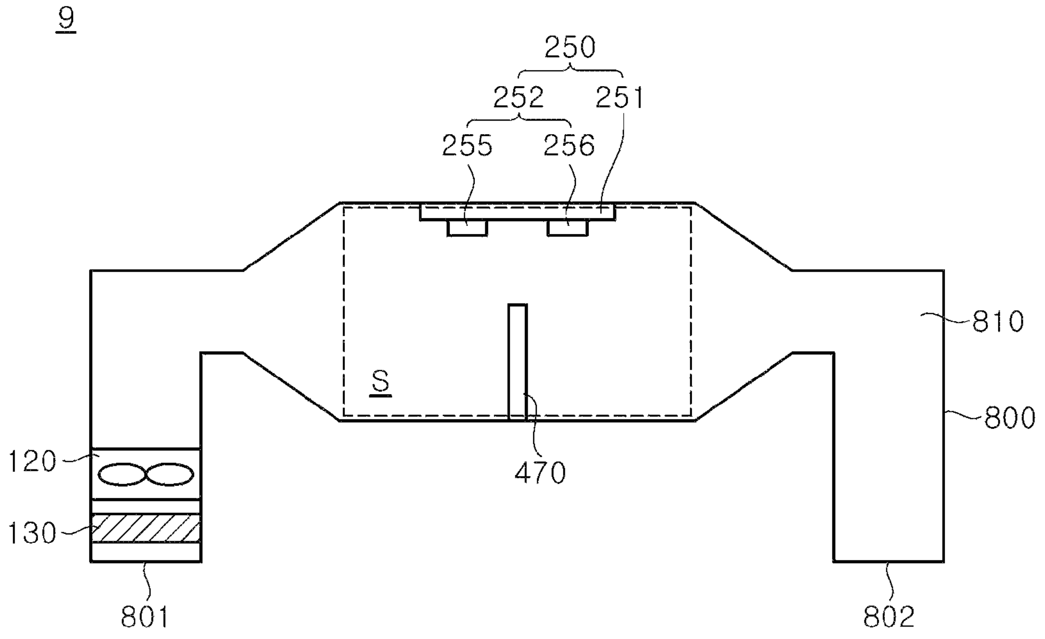
FIG. 9 is a view of a fluid treatment apparatus according to a ninth exemplary embodiment.

FIG. 9 is a view of a fluid treatment apparatus according to a ninth exemplary embodiment.

A fluid treatment apparatus 9 according to the ninth exemplary embodiment may include a pipe 810, a fan 120, a filter 130, a guide 470, and a light source module 250.

In the fluid treatment apparatus 9 according to this exemplary embodiment, the pipe 810 may have a structure in which the sterilization area S has a larger cross-sectional area than the inlet 801 and the outlet 802. In the fluid treatment apparatus 9 according to this exemplary embodiment, the guide 470 is formed in the sterilization area S and faces the light source module 250.

Referring to FIG. 9, the light source module 250 is disposed on an upper inner wall of the pipe 810 and emits light downwards. In addition, the guide 470 is disposed on a lower inner wall of the pipe 810 and extends upwards. The light source module 250 is separated from the guide 470.

The light source module 250 may include multiple light sources 252. For example, the light source module 250 may include a first light source 255 and a second light source 256.

The first light source 255 may be disposed between a start point of sterilization area S and the guide 470. Accordingly, the first light source 255 may emit light towards a region from the start point of the sterilization area S to the guide 470.

The second light source 256 may be disposed between the guide 470 and an end portion of the sterilization area S. Accordingly, the second light source 256 may emit light towards a region from the guide 470 to the end portion of the sterilization area S.

With the structure of the pipe 810, the fluid treatment apparatus 9 according to this exemplary embodiment can reduce the flow rate of the fluid. In addition, the fluid treatment apparatus 9 according to this exemplary embodiment can increase a movement distance of the fluid in the sterilization area S through the guide 470. Further, in the fluid treatment apparatus 9 according to this exemplary embodiment, the light source module 250 may be disposed on the upper inner wall of the pipe to reduce the distance between the light source module 250 and the fluid passing through the sterilization area S.

Accordingly, the fluid treatment apparatus 9 according to this exemplary embodiment can improve sterilization efficiency with respect to the fluid by reducing the flow rate of the fluid while increasing the movement distance of the fluid and increasing the intensity of light emitted to the fluid.

In the fluid treatment apparatuses 8 and 9 shown in FIG. 8 and FIG. 9, the light source module 250 is illustrated as being disposed on the upper inner wall of the pipe 810 and emits light downwards. However, the inventive concepts are not limited thereto.

In the fluid treatment apparatuses 8 and 9 shown in FIG. 8 and FIG. 9, the light source module 250 may be disposed across the flow channel 810, as in the fluid treatment apparatus 2 shown in FIG. 2. In these exemplary embodiments, the flow rate of the fluid may be controlled by the substrate of the light source module 250, thereby improving sterilization efficiency.

Figure 10:
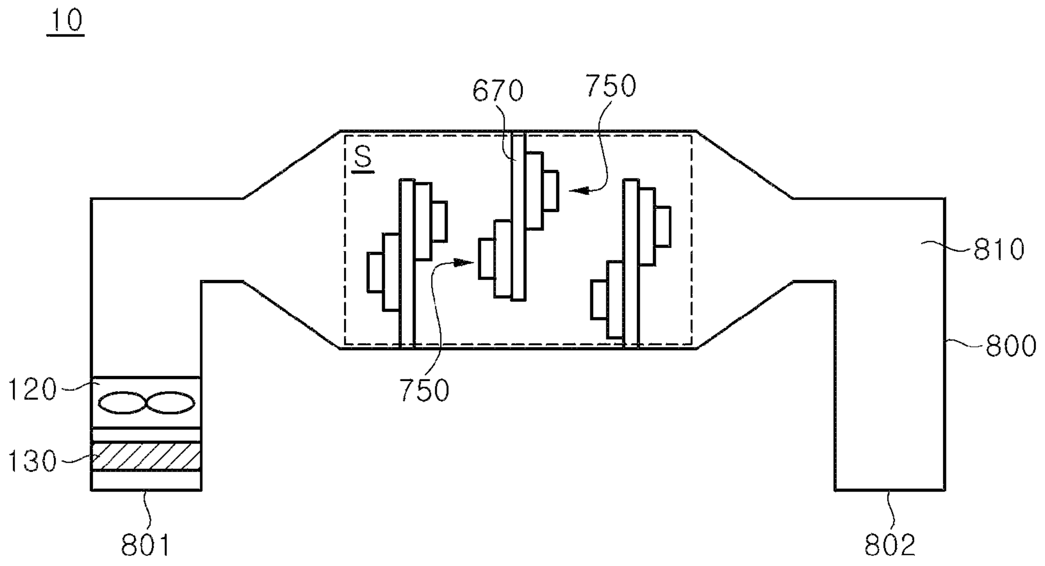
FIG. 10 is a view of a fluid treatment apparatus according to a tenth exemplary embodiment.

FIG. 10 is a view of a fluid treatment apparatus according to a tenth exemplary embodiment.

A fluid treatment apparatus 10 according to the tenth exemplary embodiment may include a pipe 810, a fan 120, a filter 130, guides 670, and light source modules 750.

The fluid treatment apparatus 10 according to the tenth exemplary embodiment has the same structure as the fluid treatment apparatus 80 according to the ninth exemplary embodiment in terms of the structure of the pipe 810, except for the number and arrangement of the guides 670 and the light source modules 750.

Referring to FIG. 10, the fluid treatment apparatus 10 according to this exemplary embodiment can increase the residence time of the fluid in the sterilization area S by increasing a flow path of the fluid through the multiple guides 670 and generating a vortex. Accordingly, the fluid treatment apparatus 10 according to this exemplary embodiment can improve sterilization efficiency by increasing the exposure time of the fluid to light.

Further, in the fluid treatment apparatus according to this exemplary embodiment, the pipe 810 may be provided with multiple guides 670, each of which may be provided with multiple light source modules 750.

The light source modules 750 may be disposed on opposite surfaces of each of the guides 670, respectively. Here, the light source modules 750 arranged to emit light towards the same region may be arranged in consideration of a beam angle. For example, the light source modules 750 may be alternately arranged so as to minimize the irradiation overlapping region of light emitted therefrom. Accordingly, the fluid treatment apparatus 10 according to this exemplary embodiment can improve sterilization efficiency through improvement in uniformity of light emitted to the entirety of the sterilization area S.

Figure 11:
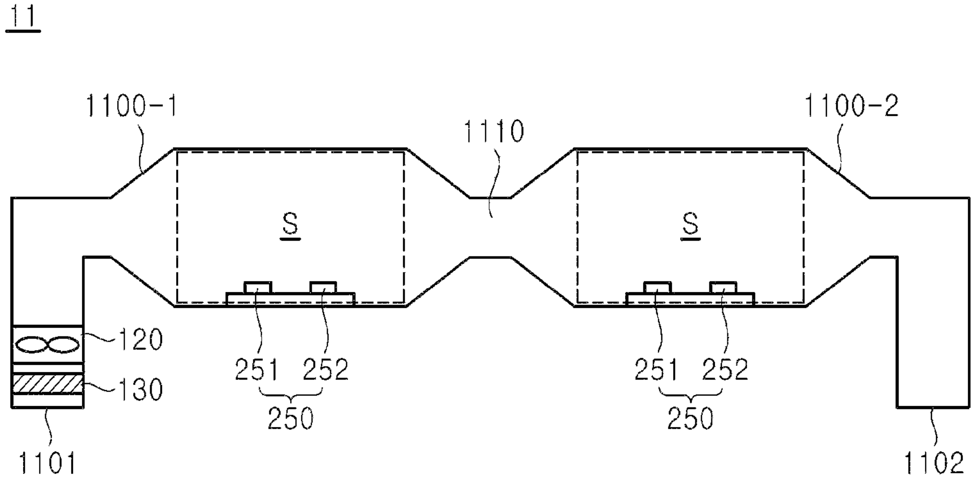
FIG. 11 is a view of a fluid treatment apparatus according to an eleventh exemplary embodiment.

FIG. 11 is a view of a fluid treatment apparatus according to an eleventh exemplary embodiment.

A fluid treatment apparatus 11 according to the eleventh exemplary embodiment may include a pipe, a fan 120, a filter 130, and light source modules 250.

According to this exemplary embodiment, the pipe includes a first pipe 1100-1 and a second pipe 1100-2.

Each of the first pipe 1100-1 and the second pipe 1100-2 may have the same structure as the pipe 810 of the fluid treatment apparatus 8 shown in FIG. 8. The first pipe 1100-1 may be connected to the second pipe 1100-2. That is, an outlet of the first pipe 1100-1 may be connected to an inlet of the second pipe 1100-2. Accordingly, in the fluid treatment apparatus 11 according to this exemplary embodiment, an inlet 1101 may define the inlet of the first pipe 1100-1 and an outlet 1102 may define the outlet of the second pipe 1100-2.

With this structure of the pipe, the fluid treatment apparatus 11 according to this exemplary embodiment can increase the residence time of the fluid in the sterilization area S and a flow channel 1110. For detailed description of this structure, refer to description of the pipe 810 of the fluid treatment apparatus 11 according to the eighth exemplary embodiment.

According to this exemplary embodiment, the first pipe 1100-1 and the second pipe 1100-2 each having a structure capable of increasing the residence time of the fluid are continuously arranged, thereby further increasing the residence time of the fluid in the pipe.

Further, each of the first pipe 1100-1 and the second pipe 1100-2 is provided with the light source module 250, whereby the fluid can be exposed to light in the first pipe 1100-1 and the second pipe 1100-2.

As such, the fluid treatment apparatus 11 according to this exemplary embodiment can improve sterilization efficiency by increasing the residence time of the fluid, the flow path of the fluid, and the exposure time of the fluid to light.

Referring to FIG. 11, the fluid treatment apparatus 11 according to this exemplary embodiment includes two pipes connected to each other. However, the inventive concepts are not limited thereto, and may include a greater number of pipes connected to one another in other exemplary embodiments.

In addition, the fluid treatment apparatus 11 according to this exemplary embodiment may further include at least one guide 470 described in the above exemplary embodiments.

Further, in the fluid treatment apparatus 11 according to this exemplary embodiment, the guide 470 and the light source module 250 in the sterilization area S may be disposed as the guide 670 and the light source module 750 of the fluid treatment apparatus 10 shown in FIG. 10.

Figure 12:
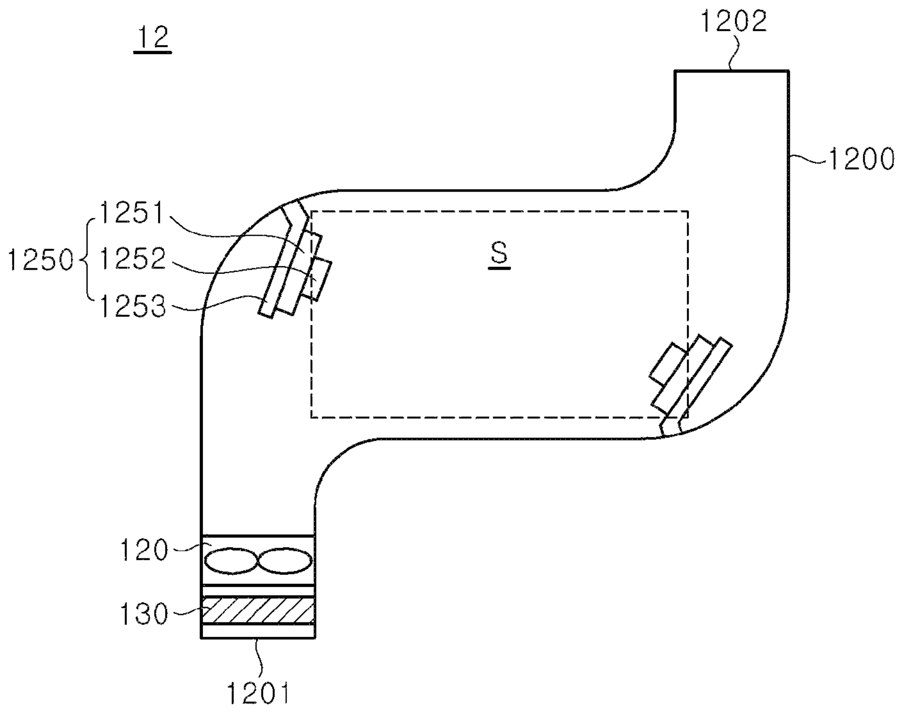
FIG. 12 is view of a fluid treatment apparatus according to a twelfth exemplary embodiment.

FIG. 12 is an exemplary view of a fluid treatment apparatus according to a twelfth exemplary embodiment.

A fluid treatment apparatus 12 according to the twelfth exemplary embodiment may include a pipe 1200, a fan 120, a filter 130, and light source modules 1250.

In the fluid treatment apparatus 12 according to this exemplary embodiment, an inner wall of the pipe 1200 has a curved surface formed on at least a portion thereof. Referring to FIG. 12, the pipe 1200 may be formed to have at least two bent portions. In addition, the pipe 1200 may include a sterilization area S in each of the first and second bent portions.

Referring to FIG. 12, an inlet 1201 of the pipe 1200 faces in a different direction than an outlet 1202 of the pipe 1200. However, the inventive concepts are not limited to this structure of the pipe 1200.

According to this exemplary embodiment, the fluid flowing along the inner wall of the pipe 1200 generates a vortex in the sterilization area S while moving along the curved surface of the inner wall of the pipe 1200. The vortex increases the residence time of the fluid in the sterilization area S.

In the fluid treatment apparatus 12 according to this exemplary embodiment, multiple light source modules 1250 may be arranged to emit light towards the sterilization area S. For example, the multiple light source modules 1250 may be disposed on the bent portions to emit light in a diagonal direction, as shown in FIG. 12.

According to this exemplary embodiment, each of the light source modules 1250 may include a substrate 1251, a light source 1252, and a substrate holder 1253.

With the light source 252 mounted on the substrate 1251, the substrate holder 1253 secures the substrate 1251 to the bent portion in a diagonal direction. Accordingly, the light source module 1250 may be disposed on the bent portion by the substrate holder 1253 to stably emit light towards the sterilization area S.

Further, the substrate holder 1253 allows adjustment in angle at a portion of the substrate holder 1253 secured to the inner wall, and at a portion of the substrate holder 1253 on which the substrate 1251 is mounted. Thus, a light irradiation region of the light source module 1250 may be adjusted through angle adjustment by the substrate holder 1253.

As such, the fluid treatment apparatus 12 according to this exemplary embodiment can increase the exposure time of the fluid to light through the structure of the pipe 1200 configured to generate a vortex of the fluid in the sterilization area S. Accordingly, the fluid treatment apparatus 12 according to this exemplary embodiment can improve sterilization efficiency.

Figure 13:
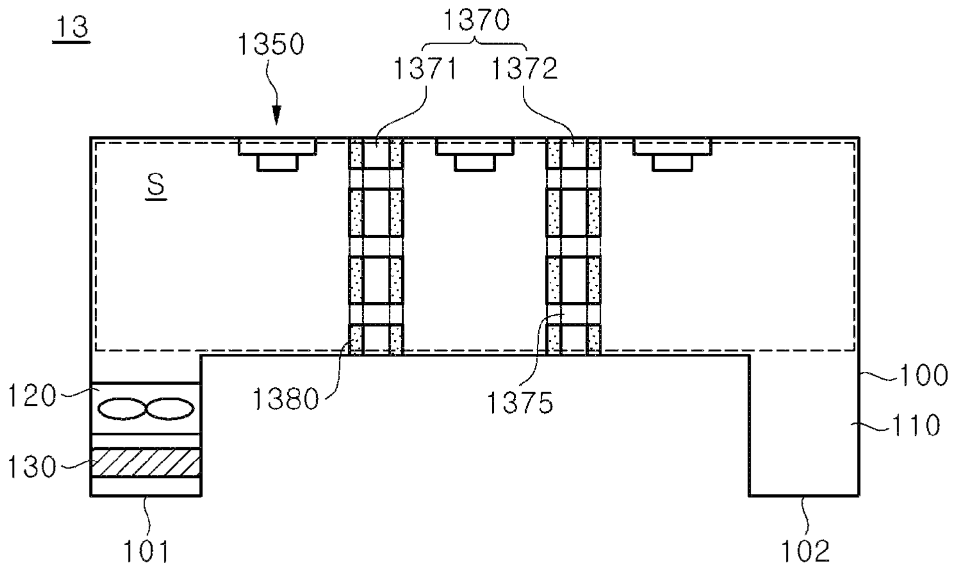
FIG. 13 is a view of a fluid treatment apparatus according to a thirteenth exemplary embodiment.

FIG. 13 is a view of a fluid treatment apparatus according to a thirteenth exemplary embodiment.

A fluid treatment apparatus 13 according to the thirteenth exemplary embodiment may include a pipe 100, a fan 120, filters 130, 1380, guides 1370, and light source modules 1350.

The fluid treatment apparatus 13 according to this exemplary embodiment may include a multiple guide 1370. For example, the fluid treatment apparatus 13 may include a first guide 1371 and a second guide 1372.

According to this exemplary embodiment, each of the first guide 1371 and the second guide 1372 may have an outer surface closely contacting the inner wall of the pipe 100 that defines the sterilization area S. In addition, each of the first guide 1371 and the second guide 1372 may be formed with multiple through-holes 1375.

That is, as shown in FIG. 13, the first guide 1371 and the second guide 1372 may block the flow channel 110 of the pipe 100 and the through-holes 1375 of the guides 1370 may act as the flow channel 110.

Accordingly, since the fluid collides with the guides 1370 or passes through the flow channel 110 narrowed by the through-holes 1375, the residence time of the fluid in the sterilization area S can be increased.

Further, the first guide 1371 and the second guide 1372 may be disposed such that the through-holes 1375 of the first guide 1371 alternate with the through-holes 1375 of the second guide 1372.

Accordingly, the length of the flow path of the fluid can be increased through alternate arrangement of the through-holes 1375 in the first guide 1371 and the second guide 1372.

The light source modules 1350 may be disposed on an upper inner wall of the pipe 100 defining the sterilization area S. Accordingly, the light source modules 1350 may emit light towards the fluid passing through the first guide 1371 and the second guide 1372. Thus, the fluid treatment apparatus 13 according to this exemplary embodiment can improve sterilization efficiency with respect to the fluid by increasing the exposure time of the fluid to light through the structures of the first guide 1371 and the second guide 1372.

Further, according to this exemplary embodiment, each of the first guide 1371 and the second guide 1372 may include the filter 1380 that filters out contaminants contained in the fluid.

For example, each of the first guide 1371 and the second guide 1372 may be provided with the filter 1380 formed with multiple through-holes 1375. In addition, opposite surfaces of each of the first guide 1371 and the second guide 1372 may include a component capable of adsorbing the contaminants in the fluid.

Accordingly, while the fluid passes through the first guide 1371 and the second guide 1372, the contaminants in the fluid may be adsorbed to the filter 1380. Since the contaminants are adsorbed to the filters 1380 of the first guide 1371 and the second guide 1372, the contaminants can be removed through exposure to light emitted from the light source module 1350 for a long period of time.

As such, the fluid treatment apparatus 13 according to this exemplary embodiment increases the exposure time of the fluid to light and allows the contaminants to be exposed to light for a long period of time through the guides 1370, thereby improving sterilization efficiency with respect to the fluid.

In this exemplary embodiment, the guides 1370 are formed with the filters 1380. However, it is contemplated that the filters 1380 may also be applied to the fluid treatment apparatus 13 according to the above exemplary embodiment including the guides 1370.

Figure 14:
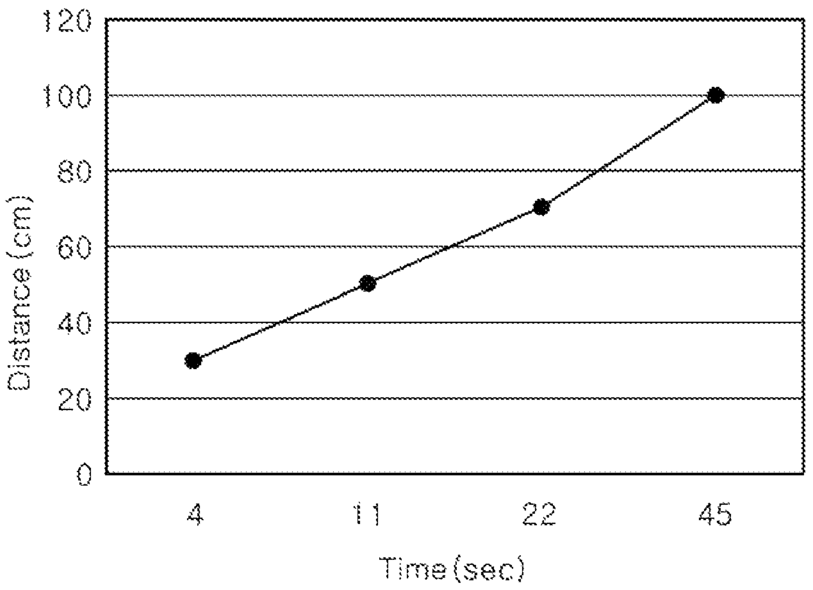
FIG. 14 is a graph depicting sterilization efficiency of a light source module included in a fluid treatment apparatus according to an exemplary embodiment.

FIG. 14 is a graph depicting sterilization efficiency of a light source module included in a fluid treatment apparatus according to an exemplary embodiment.

According to this exemplary embodiment, the light source module may perform sterilization with different types of light depending on the type of contaminant, the purpose of use, the type of fluid, and the like.

For example, the light source module may be provided with a light source emitting UVC, UVB, or UVA depending on the sterilization purpose. In addition, the light source module may include a light source emitting light having a peak wavelength in the range of 400 nm to 430 nm depending on the sterilization purpose.

The light source of the light source module may be a light emitting diode.

TABLE 1

| Time (sec) | Distance (cm) |
|---|---|
| 4 | 30 |
| 11 | 50 |
| 22 | 70 |
| 45 | 100 |

FIG. 14 is a graph depicting results shown in Table 1. Table 1 and FIG. 14 show irradiation time and distance from the light source module that can achieve sterilization of about 99.9% of contaminants by UVC.

When the light source module emits UVC, 99.9% of contaminants within a distance of 30 cm from the light source module can be sterilized in about 4 seconds.

In addition, when the light source module emits UVC, 99.9% of contaminants within a distance of 50 cm from the light source module can be sterilized in about 11 seconds.

In addition, when the light source module emits UVC, 99.9% of contaminants within a distance of 70 cm from the light source module can be sterilized in about 22 seconds.

In addition, when the light source module emits UVC, 99.9% of contaminants within a distance of 100 cm from the light source module can be sterilized in about 45 seconds.

As such, the area in which sterilization is performed may also be increased in proportion to the time for which sterilizing light is emitted.

Accordingly, sterilization efficiency may be controlled by adjusting at least one of a period of time for which the light source module emits light and the distance between a light source module and a contaminant.

Such a light source module may be the light emitting module applied to the first to thirteenth exemplary embodiments.

Figure 15:
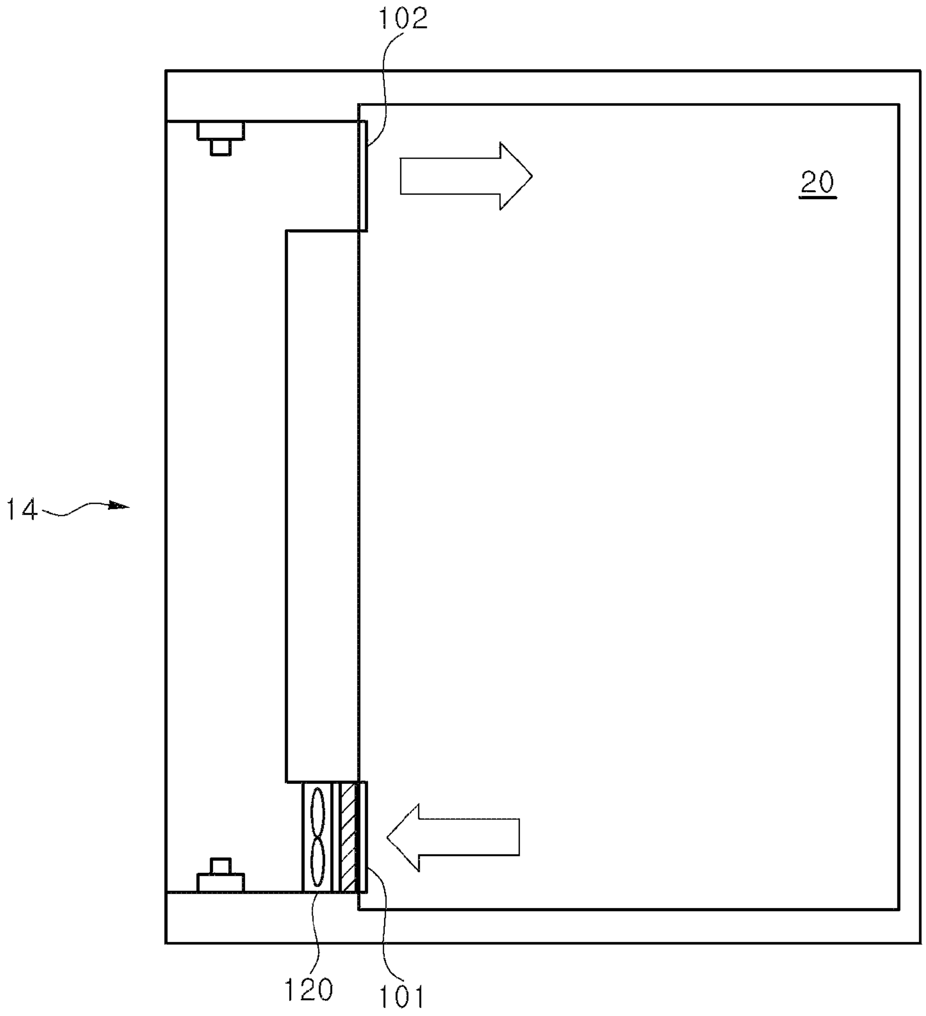
FIG. 15 is a view of a fluid treatment apparatus according to an exemplary embodiment provided to a fluid treatment space.

FIG. 15 is a view of a fluid treatment apparatus according to an exemplary embodiment.

Referring to FIG. 15, the fluid treatment apparatus 14 is schematically shown. The fluid treatment apparatus 14 shown in FIG. 15 may be one of the fluid treatment apparatus according to the exemplary embodiments described above.

The fluid treatment space 20 is placed outside the fluid treatment device 14, and may be a space 20 in which air or water flows or is stored. That is, the fluid may be a gas like air or a liquid like water. For example, the fluid treatment space 20 may be an indoor space requiring air purification.

In general, since contaminants are heavier than air, the contaminants may be concentrated on the floor of the indoor space.

Referring to FIG. 15, the inlet 101 of the fluid treatment apparatus 14 may be placed at a lower portion of the fluid treatment space 20. The outlet 102 of the fluid treatment apparatus 14 may be placed at an upper portion of the fluid treatment space 20.

Accordingly, the fluid treatment apparatus 14 according to the exemplary embodiment may perform sterilization by suctioning air at the lower portion of the fluid treatment space 20, on which contaminants are concentrated, through the fan 120. In addition, the fluid treatment apparatus 14 may discharge the sterilized air to the upper portion of the fluid treatment space 20.

The fluid treatment apparatus according to the exemplary embodiment may be arranged in the fluid treatment space to perform sterilization after suctioning contaminants concentrated on the floor, thereby improving sterilization efficiency of the fluid treatment space.

Further, the fluid treatment apparatus according to the exemplary embodiment can prevent deterioration in sterilization efficiency while minimizing variation in size by adopting the guide and the pipe configured to increase the exposure time of the fluid to light. That is, the fluid treatment apparatus according to the exemplary embodiment can sterilize the fluid without deterioration in sterilization efficiency even when the amount of the fluid or the area of the fluid treatment space is increased.

The fluid treatment apparatus according to the exemplary embodiments can improve sterilization efficiency through increase in exposure of fluid to sterilizing light.

The fluid treatment apparatus according to the exemplary embodiments can improve sterilization efficiency with respect to a fluid containing contaminants by sterilizing the fluid after suctioning the fluid from a lower portion of a fluid treatment space.

Although certain embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

The invention claimed is:

1. A fluid treatment device comprising:

a pipe having an inlet and an outlet through which a fluid is transferred, the pipe being formed with a flow channel connecting the inlet to the outlet to define a sterilization area therein;

a fan having rotating elements, such that rotation of the rotating elements control a flow of the fluid and force the fluid to flow from the inlet of the pipe to the outlet thereof; and at least one light source module comprising a light source configured to emit sterilizing light towards the sterilization area of the pipe, and a substrate on which the light source is mounted, wherein:

the inlet of the pipe is disposed adjacent to a bottom surface of an external space of the pipe, the outlet of the pipe is disposed adjacent to the bottom surface of the external space of the pipe at a different location than the inlet of the pipe, the pipe comprises a bent portion such that a flow direction of the fluid passing through the inlet and the outlet of the pipe is different from a flow direction of the fluid passing through the sterilization area, a length of the sterilization area is greater than a diameter of the sterilization area, and the fan is positioned in the bent portion where the flow direction of the fluid passing through the inlet and the outlet of the pipe is different from the flow direction of the fluid passing through the sterilization area.

2. The fluid treatment apparatus according to claim 1, wherein the pipe is bent between the inlet and the sterilization area and between the sterilization area and the outlet.

3. The fluid treatment apparatus according to claim 2, wherein the at least one light source module is respectively disposed on at least one of an inner wall of the pipe facing the sterilization area in a region of the pipe having the inlet, and an inner wall of the pipe facing the sterilization area in a region of the pipe having the outlet.

4. The fluid treatment apparatus according to claim 2, wherein:

the substrate of the light source module is disposed across the flow channel of the pipe;

the light source of the light source module is configured to emit light in a direction opposite to a flow direction of the fluid; and the fluid is configured to pass through a passage formed by the substrate to flow towards the outlet of the pipe.

5. The fluid treatment apparatus according to claim 2, wherein the light source module is provided to the sterilization area to be disposed on at least one of an upper inner wall and a lower inner wall of the pipe defining the sterilization area.

6. The fluid treatment apparatus according to claim 2, wherein the pipe further comprises at least one guide formed in the sterilization area to change a flow path of the fluid, the guide being formed on an upper inner wall of the pipe to extend downwards therefrom or on a lower inner wall of the pipe to extend upwards therefrom.

7. The fluid treatment apparatus according to claim 6, wherein the guide is provided in plural in the pipe, and the guides are alternately provided in the sterilization area on the upper inner wall of the pipe and on the lower inner wall of the pipe.

8. The fluid treatment apparatus according to claim 6, wherein the guide has an outer surface closely contacting the inner wall of the pipe defining the sterilization area, and is formed with multiple through-holes penetrating opposite surfaces thereof, such that the fluid is configured to pass through the through-holes of the guide.

9. The fluid treatment apparatus according to claim 8, wherein the guide is provided in plural in the pipe, and the through-holes of one guide alternate with the through-holes of another guide along the flow direction.

10. The fluid treatment apparatus according to claim 6, wherein the guide comprises a light transmitting material.

11. The fluid treatment apparatus according to claim 6, wherein:

the substrate of the light source module is disposed across the flow channel of the pipe;

the light source of the light source module is configured to emit light in a direction opposite to a flow direction of the fluid; and the fluid is configured to pass through a passage formed by the substrate to flow towards the outlet of the pipe.

12. The fluid treatment apparatus according to claim 6, further comprising:

a filter formed on the guide and filtering out contaminants in the fluid.

13. The fluid treatment apparatus according to claim 6, wherein the light source module is disposed at each of both sides of the guide.

14. The fluid treatment apparatus according to claim 2, wherein the sterilization area of the pipe has a larger cross-sectional area than the cross-sectional area of the inlet and the outlet of the pipe.

15. The fluid treatment apparatus according to claim 14, wherein the pipe is provided in plural and the outlet of one pipe is connected to the inlet of another pipe.

16. The fluid treatment apparatus according to claim 2, wherein:

the pipe comprises at least two bent portions each having a curved surface on at least a portion of an inner wall thereof;

the sterilization area is formed between the two bent portions; and the light source module is placed diagonally on the curved surface to emit light towards the sterilization area.

17. The fluid treatment apparatus according to claim 16, wherein:

the light source module further comprises a substrate holder securing the substrate to the curved surface in a diagonal direction; and the substrate holder has one portion secured to the curved surface of the pipe and another portion on which the substrate is mounted.

18. The fluid treatment apparatus according to claim 17, wherein an angle of the one portion and the other portion of the substrate holder is adjustable with respect to the curved surface.

19. The fluid treatment apparatus according to claim 1, wherein the fan is disposed at the bent portion adjacent the inlet of the pipe.

20. The fluid treatment apparatus according to claim 19, further comprising:

a filter respectively disposed on at least one of a front end and a rear end of the fan.

* * * * *